United States Patent [19]

De Noble et al.

[11] Patent Number: 5,171,745
[45] Date of Patent: Dec. 15, 1992

[54] METHOD OF TREATING NEUROLOGICAL DYSFUNCTION USING NEUTROTRANSMITTER ENHANCERS

[75] Inventors: Kimi F. De Noble; Victor J. De Noble, both of Newark; Richard A. Earl, Wilmington, all of Del.; Melvyn J. Myers, Middletown, Conn.; Victor J. Nickolson, Hermelynengrees, Netherlands

[73] Assignee: Du Pont Merck Pharmaceutical Company, Wilmington, Del.

[21] Appl. No.: 552,216

[22] Filed: Jul. 13, 1990

[51] Int. Cl.$^5$ .............................. A61K 31/44
[52] U.S. Cl. ..................... 514/333; 514/339
[58] Field of Search ................. 514/333, 339

[56] References Cited

U.S. PATENT DOCUMENTS

| | | | |
|---|---|---|---|
| 4,760,083 | 7/1988 | Myers et al. | 514/313 |
| 4,876,259 | 10/1989 | Myers et al. | 514/313 |

FOREIGN PATENT DOCUMENTS

| | | |
|---|---|---|
| 279990 | 8/1988 | European Pat. Off. |
| 311010 | 4/1989 | European Pat. Off. |

OTHER PUBLICATIONS

Chem. Abst. 77-70232r (1972).
Chem. Abst. 90-80738t (1979).
Cook et al., Drug Devel. Res. 19:301-314 (1990).
Nickolson et al., Drug Devel. Res. 19:285-300 (1990).
Francis et al., New England J. Med. 313:7 (1985).
Sims et al., J. Neurochem. 38:488-492 (1982).
Davis et al., Psychopharm. Bulletin 19:451-453 (1983).
Moos et al., Medicinal Res. Rev. 8:353-391 (1988).
Davis et al., New Eng. J. Med. 301:946 (1988).
Summers et al., New Eng. J. Med. 315:1241-1245 (1986).
DeNoble et al., Pharmacol. Biochem. Behav. 36:957-961 (1990).
Palmer et al., Ann. Neurol. 23:616-620 (1988).
Davies et al., Lancet 2:1403 (1976).
Altman et al., Pharmacol. Biochem. Behav. 28:353-359 (1987).
Strek et al., Pharmacol. Biochem. Behav. 33:241-244 (1989).
Bradley et al., Neuropharmacology 25:563-576 (1986).
Barnes et al., Pharmacol. Biochem. Behav. 35:955-962 (1990).
Barnes et al., Nature 338:762-763 (1989).

*Primary Examiner*—S. J. Friedman
*Attorney, Agent, or Firm*—Blair Q. Ferguson; Lynne Christenbury

[57] ABSTRACT

This disclosure relates to a method of treating a neurological dysfunction in a mammal using a combination of at least one neurotransmitter enhancer and at least one serotonin receptor antagonist.

2 Claims, No Drawings

METHOD OF TREATING NEUROLOGICAL DYSFUNCTION USING NEUTROTRANSMITTER ENHANCERS

FIELD OF THE INVENTION

This invention relates to a method of treating neurological dysfunction in a mammal and, more particularly, to method which utilizes a therapeutically effective amount of a combination of: (i) at least one neurotransmitter enhancer and (ii) at least one serotonin receptor antagonist.

BACKGROUND OF THE INVENTION

There is a steadily growing need for effective treatment of neurological dysfunction which produces cognitive and neurological deficiencies. Many of these diseases are caused by degenerative changes in the nervous system. Typically, the incidence of these diseases increases as a function of age. Deficits in the synthesis and release of acetylcholine in the brain are generally thought to be related to cognitive impairment (see Francis et al., *New England J. Med.*. 313, 7, 1985), whereas neurological deficits (e.g., Parkinsonian symptoms) and mood/mental changes may be related to impairment of d.opaminergic and serotonergic systems, respectively. Other neurological deficits (e.g., myasthenia gravis) are related to cholinergic deficiencies in the peripheral nervous system.

Treatment strategies employed hitherto encompass vasoactive drugs like vincamine and pentoxifylline; "metabolic enhancers" like ergoloid mesylates, piracetam and naftidrofuryl; neurotransmitter precursors like l-DOPA, choline and 5-hydroxytryptamine (5HT); transmitter metabolizing enzyme inhibitors like physostigmine (PH); and neuropeptides like adrenocorticotropic hormone and vasopressin-related peptides. These treatment strategies generally have failed to produce clinically significant improvements (Hollister et al., *Drugs*, 29, 483, 1985) similar to the improvements obtained by treating Parkinson's disease with 1-dopa or treating myasthenia gravis with cholinesterase inhibitor. Enhancement of the residual function of the affected systems by enhancing the stimulus-induced release of neurotransmitters provides an alternative to treat these multiple symptoms. Theoretically, such an enhancement would improve the signal-to-noise ratio during chemical transmission of information, thereby reducing deficits in processes related to cognition, neurological function, and mood regulation.

Recent findings suggest that the cerebral cholinergic system may be involved in the senile decline of cerebral function. Cortical acetylcholine (ACh) synthesis and release decline as a function of age in experimental animals as described by (Gibson et al., *J. Neurochem.*, 38, 488, 1982). The primary deficit in patients suffering from Alzheimer's disease is one of cholinergic origin. There is a marked reduction in the number of cholinergic cell bodies in the nucleus basalis of Meynert resulting in a decrease of choline acetyltransferase activity, acetylcholinesterase activity, and acetylcholine synthesis in the cortical and hippocampal projection areas as described by (Perry et al., *J. Neuro.*, 40, 503, 1983). Furthermore, the noradrenergic, the dopaminergic, and the serotonergic systems also appear to be deficient in a majority of patients suffering from Alzheimer's disease (Davis et al., *Physchopharm, Bulletin*, 19, 451, 1983).

Researchers have attempted to enhance the neuronal function by using drugs which enhance endogenous stimulus-induced neurotransmitter release which would result in an increase of the amount of neutrotransmitter solely when its release is triggered by excitation of the cholinergic neuron. Such action should result in an improvement of the signal-to-noise ratio during transmission in the cholinergic function without the ACh overload toxicity that is typical for cholinesterase inhibitors, or without the distortion of temporal patterns in cholinergic transmission, as caused by direct cholinergic agonists.

Cognitive deficits resulting from neuropathological brain changes or normal aging are most likely due to alterations in multiple neurotransmitter systems. Cholinergic, noradrenergic, dopaminergic, and peptidergic neurotransmitter systems have all been implicated in the mediation of learning and memory decline associated with aging (e.g., Olton et al., *Ann, New York Acad. Sci.*, 444, 1985; Moos et al., *Med. Res. Rev.*, 8, 353–392, 1988). A majority of research has focused on the cholinergic nervous system with particular reference to cognitive deficits resulting from Alzheimer's disease (AD).

As a result a number of drugs that increased brain cholinergic activity have been used clinically to treat various neurological disorders resulting in cognitive impairment (Moos et al., *Med. Res. Rev.*, 8, 353–392, 1988). Attempts to increase acetylcholine (ACh) synthesis by treatment with ACh precursor choline or lecithin have not been very successful. More recent research focused upon the use of muscarinic agonists, or cholinesterase inhibitors (AChE) such as physostigmine (PH) and tetrahydroacridine (THA), both of which increase ACh by inhibiting its metabolic degradation after release. Recent reports of limited success in reducing the cognitive deficits and symptoms of dementia in AD by treatment with AChE inhibitors such as PH (Davis et al., *N. Eng. J. Med.*, 301, 946, 1979) and THA (Summers et al., *N. Eng. J. Med.*, 315, 1241–1245, 1986) have renewed interest in the search for other cholinomimetic agents that have similar mechanisms of action. However, the potential therapeutic application of AChE inhibitors is limited by several factors. The most predominant one being side effects resulting from chronic post-synaptic stimulation.

As an alternative to inhibiting the AChE activity resulting in increased ACh with abnormal enzymatic degeneration, a search was undertaken to identify ACh release enhancers. Compounds which can be used to enhance the neuronal function are disclosed in U.S. Pat. No. 4,760,083, issued to Myers et al. on July 26, 1988, U.S. Pat. No. 4,876,259, issued to Myers et al. on Oct. 24, 1989, and in coassigned application Ser. No. 07/234,382, filed Aug. 23, 1988 (European Patent Application Publication No. 0311010, published Apr. 12, 1989). 3,3-Disubstituted indolines are described which enhance stimulus-induced release of neurotransmitters, specifically acetylcholine, as well as, dopamine and serotonin. These compounds were screened for this activity by evaluating their effect on the release of a neurotransmitter, such as acetylcholine (ACh), from rat cerebral cortex slices using a superfusion procedure described by Mulder et al., *Brain Res.*, 70, 372, 1974, as modified according to Nickolson et al., *Naunyn Schmied. Arch. Pharmacol.*, 319, 48, 1982.

Compounds with such activity can be useful in treating cognitive and/or neurological deficiencies and/or mood or mental disturbances such as found in patients suffering from degenerative nervous system disorders, for example, Alzheimer's disease, Parkinson's disease, senile-dementia, multi-infarct dementia, Huntington's disease, mental retardation, and myasthenia gravis.

The compounds disclosed in U.S. Pat. Nos. 4,760,083 and 4,876,259, include 3,3-bis(4-pyridinylmethyl)-1-phenylindolin-2-one (DuP 996), which has been shown to enhance stimulated ACh release from rat cortical, hippocampal and striatal slices in vitro and from the cortex of awake freely moving rats in vivo without changes in AChE activity (Nickolson et al., *Drug Develop, Research*, 19/3, 285–300, 1990). In addition, previous studies have shown that DuP 996 protects against hypoxia-induced amnesia of a passive avoidance (PA) response in rats at a dose range of 0.01 to 0.1 mg/kg s.c. (Cook et al., *Drug Develop, Research*, 19, 301–314, 1990).

It appears that hypo-cholinergic function results in dementia, but dementia is not always due to a deficit in cholinergic transmission. It can be mediated by other neurotransmitter systems. It is well established that there is a decrease in forebrain 5-hydroxytryptamine (5HT) in the AD brain. Specifically, concentrations of 5HT and its metabolite 5-hydroxyindole acetic acid are reduced and the 5HT1- and 5HT2-receptor densities decreased in hippocampus, frontal, and temporal cortices (e.g., Palmer et al., *Ann. Neurol.*, 23, 616–620, 1988). However, the loss of serotonin innervation does not parallel the loss of cholinergic or adrenergic innervation (e.g., Davies et al., *Lancet*, 2, 1403, 1976; Adolfsson et al., *Br. J. Psychiatry*, 135, 216–223, 1979), and it may be hypothesized that the inhibitory tone that the serotonergic nervous system is suspected to have on other neurotransmitter systems would be maintained or even exaggerated (Normile et al., *Plenum Pub. Coro.*, 141–156, 1987). In that regard, 5HT antagonists would be expected to improve performance by decreasing the inhibitory control maintained on the central nervous system.

A recent series of reports has shown that a number of 5HT receptor antagonists, both non-selective (e.g., metergoline), and 5HT2-receptor selective (e.g., pirenperone, ketanserin) can enhance memory of a previously learned inhibitory response in mice (e.g., Altman et al., *Pharmacol. Biochem. Behav.*, 28, 353–359, 1987) and can reverse hypoxia-induced passive avoidance (PA) retention deficits in rats (e.g., Strek et al., *Pharmacol, Biochem. Behav.*, 33, 241–244, 1989). These studies support the notion that 5HT antagonists administered after avoidance training or after an experimentally induced memory deficit (exposure to hypoxia) can enhance retrieval in mice (e.g., Altman et al., *Pharmacol. Biochem. Behav.*, 28, 353–359, 1987) and protect rats from experimentally-induced amnesia (e.g., Strek et al., *Pharmacol. Behav.*, 33, 241–244, 1989).

European Patent Application Publication No. 279,990, published on Aug. 31, 1988, describes the use of heterocyclic 5-hydroxytryptamine antagonists for treating cognitive disorders.

SUMMARY OF THE INVENTION

This invention concerns a method of treating a neurological dysfunction in a mammal comprising administering to the mammal a therapeutically effective amount of a combination of: (a) at least one serotonin receptor antagonist, and (b) at least one neurotransmitter enhancer, said enhancer being a compound of the formula:

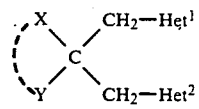

or a salt thereof;
wherein:

X and Y are taken together to form a saturated or unsaturated carbocyclic or heterocyclic first ring and the shown carbon in said ring is α to at least one additional aromatic ring or heteroaromatic ring fused to the first ring;

one of $Het^1$ or $Het^2$ is 2, 3, or 4-pyridyl or 2, 4, or 5-pyrimidinyl and the other is selected from
(a) 2, 3, or 4-pyridyl,
(b) 2, 4, or 5-pyrimidinyl,
(c) 2-pyrazinyl,
(d) 3, or 4-pyridazinyl,
(e) 3, or 4-pyrazolyl,
(f) 2, or 3-tetrahydrofuranyl, and
(g) 3-thienyl.

Compounds included within Formula (I) which are useful in the method of the invention are as follows:

(1) a compound having the formula:

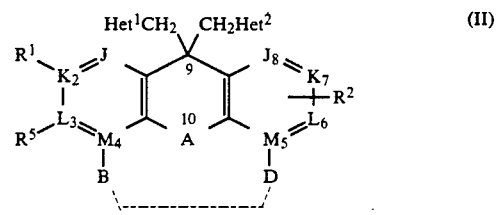

or a salt thereof, wherein:

each J, K, L and M independently are N, $CR^1$, $CR^5$ or $CR^2$ with the proviso that when either $M_4$, $M_5$ or both is N, then B, D or both cannot be $R^1$ or $R^2$;

A is $(CH_2)_n$,

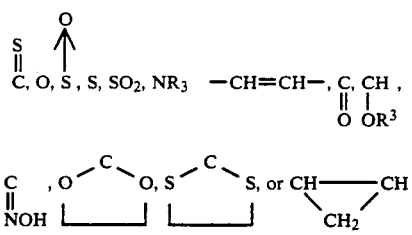

n is 0, 1, 2 or 3;

$R^1$ and $R^2$ independently are H, halo, alkyl of 1-3 carbon atoms, acyl, $OR^3$, $NO_2$, CN, $NR^3R^4$, or fluoroalkyl of 1-3 carbon atoms;

$R^3$ and $R^4$ independently are H, alkyl of 1-3 carbon atoms, or acyl;

B and D independently are $R^1$ or $R^2$ or, when A is $(CH_2)_o$ can be taken together to form —CH=CH—, or —CH$_2$—CH$_2$—;

$R^5$ independently is H, or is taken together with $R^1$ to form a 2,3- or a 3,4-fused benzo ring;

one of $Het^1$ or $Het^2$ is 2, 3, or 4-pyridyl or 2, 4 or 5-pyrimidinyl and the other is selected from:
(a) 2, 3 or 4-pyridyl,
(b) 2, 4, or 5-pyrimidinyl,
(c) 2-pyrazinyl, (d) 3, or 4-pyridazinyl,
(e) 3, or 4-pyrazolyl,
(f) 2, or 3-tetrahydrofuranyl, and
(g) 3-thienyl;
(2) a compound having the formula:

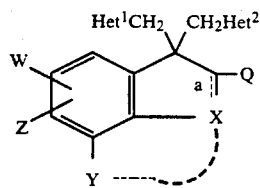

or a salt thereof,
wherein:
a is a single bond or double bond;
X independently, when a is a single bond, is O, S, $CR^1R^2$, CQ, $C(R^1)OR^3$, or $—(—CH_2—)—_n$, where n is 1, 2 or 3;
X independently, when a is a double bond, is $CR^2$ or $COR^3$;
X and Y taken together when a is a single bond is

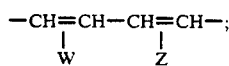

X and Y taken together when a is a double bond is

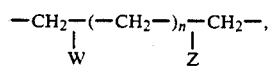

Q, when a is a single bond, is =O, =S, $H_2$, $OR^3$, =$NOR^1$,

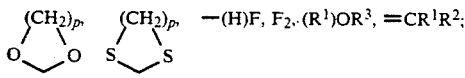

Q, when a is a double bond, is $R^2$, $OR^3$ or halo;
p is 2 or 3;
$R^1$ is H, alkyl of 1-10 carbon atoms, cycloalkyl of 3-8 carbon atoms, or

$R^2$ is $R^1$, $NO_2$, CN, $CO_2R^1$,

or halo;
$R^3$ is $R^1$ or

W, Y, Z independently are H, halo, alkyl of 1-3 carbon atoms, $OR^3$, $NO_2$, $CF_3$, fluoroalkyl, CN, or $N(R^1)_2$; and $Het^1$ and $Het^2$ are as defined in (2) above;
(3) a compound having the formula:

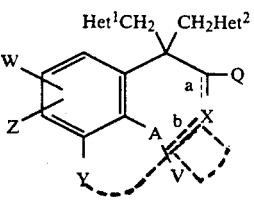

or a salt thereof, wherein:
a is a single bond or double bond;
b is a single bond or double bond, provided one of a or b is a single bond;
X independently when a and b are single bonds is O, S, $CR^1R^2$, CQ, $C(R^1)OR^3$, or $—(—CH_2—)—_n$ where n is 1, 2 or 3, $N(CH_2)_pR^3$ where p is 0 or 1, or $NCOR^1$;
X independently when one of a or b is a double bond is $CR^2$, $COR^3$, or N;
V independently when b is a single bond is CQ;
V independently when b is a double bond is $CR^2$ or $COR^3$;
A is a single bond, $—(—CR^1—)_n—$, $—(—CR^2—)_n—$, $—X—$, $—(—CR^1—)_n—X$, $—(—CR^2—)_n—X$, where n is 1, 2 or 3; and
X is as defined above when a is a single bond;
Y and V taken together when A and b are single bond is

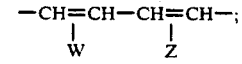

Y and V taken together when A is a single bond is $—CH_2—(—CH_2—)_m—CH_2—$ where m is 1 or 2; provided that when Y and V are connected, then V and X are not connected;
V and X taken together when b is a double bond is $—C—CH=CH—CH=CH—C—$ or $—C—(—CH_2—)-_p—C$; provided that when V and X are connected, then Y and V are not connected;
Q when a is a single bond is =O, =S, $H_2$, $OR^3$, =NOR1,

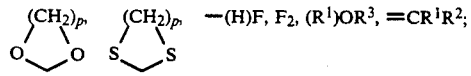

Q when a is a double bond is $R^2$, $OR^3$ or halo;
p is 2 or 3;
$R^1$ is H, alkyl of 1-10 carbon atoms, cyclo-alkyl of 3-8 carbon atoms, or

$R^2$ is $R^1$, $NO_2$, CN, $CO_xR^1$,

or halo;

$R^3$ is $R^1$ or

W, Y, Z each independently is H, halo, alkyl of 1-3 carbon atoms, $OR^3$, $NO_2$, $CF_3$, CN, or $N(R^1)_2$; and $Het^1$ and $Het^2$ are as defined in (2) above; and (4) a 3,3 disubstituted indoline having the formula:

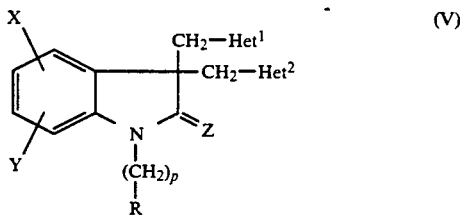

(V)

wherein:
p is 0 or 1;
Z is O or S;
R is $C_1$-$C_{10}$ alkyl, $C_3$-$C_8$ cycloalkyl, 2-pyridyl, 3-pyridyl, 4-pyridyl, or

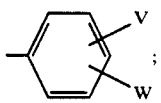

V, W, X, and Y independently are H, halo, $C_1$-$C_3$ alkyl, $OR^1$, $NO_2$, $CF_3$, CN, or $NR^1R^2$;

$R^1$ and $R^2$ independently are H or $C_1$-$C_3$ alkyl;

$Het^1$ and $Het^2$ independently are 6-membered heterocyclic aromatic rings containing one or two nitrogen atoms as part of the ring optionally substituted with one substituent selected from the group $C_1$-$C_3$ alkyl, halo, $OR^1$ or $NR^1R^2$; or an N-oxide or pharmaceutically suitable acid addition salt thereof.

In addition, the neurotransmitter release enhancer can also be a procholinergic and/or prodopaminergic compound.

DETAILED DESCRIPTION OF THE INVENTION

This invention concerns a method of treating a neurological dysfunction in a mammal comprising administering to the mammal a therapeutically effective amount of a combination of (a) at least one serotonin receptor antagonist, and (b) at least one neurotransmitter enhancer.

It has been found surprisingly and unexpectedly that co-administration of the foregoing combination produces a synergistic effect in treating neurological dysfunctions, including cognitive deficiencies as well as neurological diseases.

Serotonin receptor antagonists which can be used to practice the invention include, but are not limited to, ketanserin, methysergide, cyproheptadine, ICS 205-930 and MDL 7222 as described by Bradley et al., *Neuropharmacology*, page 563, Vol. 25 (1986); spiperone; ordansetron as described by Barnes et al., *Pharmacol, Biochem. Behav.*, page 955, Vol. 35 (1990); zacopride as described by Barnes et al., *Nature*, page 762, Vol. 338 (1989); pirenperone and mianserin as described by Strek et al., *Pharmacol, Biochem. Behav.*, page 241, Vol. 33 (1989); and quipazine, GR 65630, MDL 73147EF, and LY 278584 as described by Watling et al., *Neurotransmissions*, Vol. 5 (1989). The disclosures of the foregoing are incorporated herein by reference.

The term "neurotransmitter enhancer" means a compound whose biochemical effect results in increased neuronal and/or neurotransmitter function.

A multitude of neurotransmitter enhancers are suitable to practice the invention. There can be mentioned procholinergic compounds such as physostigmine, tetrahydroaminoacridine (THA), RS 86, 3,4-diaminopyridine, or muscarinic agonists, prodopaminergic compounds such as amantidine as well as compounds of the Formula (I) above wherein:

X and Y are taken together to form a saturated or unsaturated carbocyclic or heterocyclic first ring and the shown carbon in said ring is α to at least one additional aromatic ring or heteroaromatic ring fused to the first ring;

one of $Het^1$ or $Het^2$ is 2, 3, or 4-pyridyl or 2, 4, or 5-pyrimidinyl and the other is selected from
(a) 2, 3, or 4-pyridyl,
(b) 2, 4, or 5-pyrimidinyl,
(c) 2-pyrazinyl,
(d) 3, or 4-pyridazinyl,
(e) 3, or 4-pyrazolyl,
(f) 2, or 3-tetrahydrofuranyl, and
(g) 3-thienyl.

It is preferred that one of $Het^1$ or $Het^2$ is 2, 3, or 4-pyridyl or 2, 4, or 5-pyrimidinyl and the other is 2, 3, or 4- pyridinyl, 2, 4, or 5-pyrimidinyl, or 2 or 3- tetrahydrofuranyl.

$Het^1$ and $Het^2$ are most preferably selected from:
(a) 4-pyridinyl and 4-pyridinyl,
(b) 4-pyrimidinyl and 4-pyrimidinyl,
(c) 4-pyridinyl and 4-pyrimidinyl,
(d) 4-pyridinyl and 3-tetrahydrofuranyl.

3,3-disubstituted indolines having Formula (V) above are those wherein:
p is 0 or 1;
Z is O or S;
R is $C_1$-$C_{10}$ alkyl, $C_3$-$C_8$ cycloalkyl, 2-pyridyl, 3-pyridyl, 4-pyridyl, or

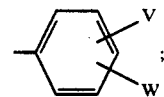

V, W, X, and Y independently are H, halo, $C_1$-$C_3$ alkyl, $OR^1$, $NO_2$, $CF_3$, CN, or $NR^1R^2$;

$R^1$ and $R^2$ independently are H or $C_1$-$C_3$ alkyl;

$Het^1$ and $Het^2$ independently are 6-membered heterocyclic aromatic rings containing one or two nitrogen atoms as part of the ring optionally substituted with one substituent selected from the group $C_1$-$C_3$ alkyl, halo, $OR^1$ or $NR^1R^2$; or an N-oxide or pharmaceutically suitable acid addition salt thereof.

Preferred compounds are those wherein:
p is 0; or
Z is O; or
X and Y are H; or
R is $CH_3$, phenyl or m-chlorophenyl; or
$Het^1$ and $Het^2$ are each pyridyl attached by a ring carbon atom.

Specifically preferred compounds of Formula (V) are:
(a) 3,3-Bis(2-pyridylmethyl)-1-phenylindolin-2-one;
(b) 3,3-Bis(3-pyridylmethyl)-1-phenylindolin-2-one;
(c) 3,3-Bis(4-pyridylmethyl)-1-phenylindolin-2-one;
(d) 3,3-Bis(4-pyridylmethyl)-1-methylindolin-2-one;
(e) 3,3-Bis(4-pyridylmethyl)-1-(3-chlorophenyl)indolin-2-one;

and pharmaceutically suitable acid addition salts thereof.

Compounds of Formula (II) include those wherein each J, K, L and M independently are N, $CR^1$, $CR^5$ or $CR^2$ with the proviso that when either $M_4$, $M_5$ or both is N, then B, D or both cannot be $R^1$ or $R^2$;

A is $(CH_2)_n$,

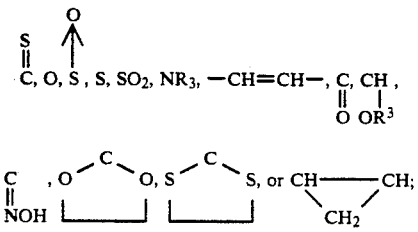

n is 0, 1, 2 or 3;

$R^1$ and $R^2$ independently are H, halo, alkyl of 2-3 carbon atoms, acyl, $OR^3$, $NO_2$, CN, $NR^3R^4$, or fluoroalkyl of 1-3 carbon atoms;

$R^3$ and $R^4$ independently are H, alkyl of 1-3 carbon atoms, or acyl;

B and D independently are $R^1$ or $R^2$, or, when A is $(CH_2)_o$ can be taken together to form —CH=CH—, or —$CH_2$—$CH_2$—;

$R^5$ independently is H, or is taken together with $R^1$ to form a 2,3- or a 3,4-fused benzo ring;

one of $Het^1$ or $Het^2$ is 2, 3, or 4-pyridyl or 2, 4 or 5-pyrimidinyl and the other is selected from:
(a) 2, 3, or 4-pyridyl,
(b) 2, 4, or 5-pyrimidinyl,
(c) 2-pyrazinyl,
(d) 3, or 4-pyridazinyl,
(e) 3, or 4-pyrazolyl,
(f) 2, or 3-tetrahydrofuranyl, and
(g) 3-thienyl.

Preferred compounds of Formula (II) are: (a) those compounds of Formula (II) where:

A is a bond, i.e., is $(CH_2)_n$ where n is 0;
B and D are $R^1$ and $R^2$;
0 to 2 of J, $K_2$, $L_3$ and $M_4$ are N and the remainder are $CR^1$ or $CR^5$; and
0 to 2 of $J_8$, $K_7$, $L_6$ and $M_5$ are N and the remainder are $CR^2$, with the proviso that when either $M_4$, $M_5$ or both is N, then B, D or both cannot be $R^1$ or $R^2$; or
$R^1$ and $R^5$ are H; or
$R^2$ is H, halo, alkyl of 1-3 carbon atoms, $OR^3$, $NH_2$, or fluoroalkyl of 1-3 carbon atoms; or
$Het^1$ and $Het^2$ are as preferred for compounds of Formula (I).

Specifically preferred compounds of Formula (II) from (a) above are:
(i) 5,5-Bis(4-pyridinylmethyl)cyclopenta[2,1-b:3,4-b']dipyridine;
(ii) 9,9-Bis(4-pyridinylmethyl)indeno-[1,2-b] pyridine;
(iii) 5,5-Bis(4-pyridinylmethyl)cyclopenta[2,1-c:3,4-c']dipyridine;
(iv) 9,9-Bis(4-pyridinylmethyl)cyclopenta[1,2-c:4,3-c']dipyridine;
(v) 9,9-Bis(4-pyridinylmethyl)cyclopenta[1,2-b:3,4-b']dipyridine.

(b) those of Formula (II) where: B and D are both H; and J, K, L and M are carbon atoms; or
A is $(CH_2)_n$ where n is 0-3,

CHOH, C=NOH, O,

$NR^3$, S, or $SO_2$; or
$R^1$ and $R^5$ are h; or
$R^2$ is H, halo, alkyl of 1-3 carbon atoms, $OR^3$, $NH_2$, or fluoroalkyl of 1-3 carbon atoms; or
$Het^1$ and $Het^2$ are as preferred for compounds of Formula (I).

Specifically preferred compounds of Formula (II) from (b) above are:
(i) 9,9-bis(4-pyridylmethyl)anthrone dihydrochloride;
(ii) 9,9-bis(4-pyridylmethyl)fluorene dihydrochloride;
(iii) 9,9-bis(4-pyridylmethyl)xanthene;
(iv) 9,9-bis(4-pyridylmethyl)-2-acetylfluorene dihydrochloride;
(v) 4,4'-[9H-fluoren-9-ylidene bis(methylene)]bispyrimidine.

(c) those of Formula (II) where:
A is a bond, i.e., is $(CH_2)n$ where n is O; and J, K, L and M are carbon atoms; or
B and D are taken together to form —CH=CH— or —$CH_2$—$CH_2$—;
$R^1$ and $R^5$ are H; or
$R^2$ is H, halo, alkyl of 1-3 carbon atoms, $OR^3$, $NH_2$, or fluoroalkyl of 1-3 carbon atoms; or
$Het^1$ and $Het^2$ are as preferred for compounds of Formula (I).

Specifically preferred compounds of Formula (II) from (c) above are:
(i) 9,9-bis(4-pyridinylmethyl)cyclopenta[def]phenanthrene;
(ii) 9,9-bis(4-pyridinylmethyl)-4,5-dihydrocyclopenta[def] phenanthrene.

Compounds of Formula (III) include those wherein a is a single bond or double bond;

X independently when a is a single bond is O, S, $CR^1R^2$, CQ, $C(R^1)OR^3$, or —($-CH_2-$)—$_n$ where n is 1, 2 or 3;

X independently when a is a double bond is $CR^2$ or $COR^3$;

X and Y taken together when a is a single bond is

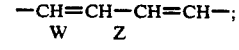

X and Y taken together when a is a double bond is

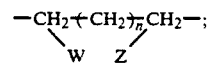

where n is 1 or 2;

Q when a is a single bond is =O, =S, H₂,

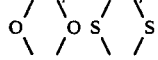

F₂, (R¹)OR³, =CR¹R²;

Q when a is a double bond is R², OR³ or halo;
R¹ is H, alkyl of 1-10 carbon atoms, cycloalkyl of 3-8 carbon atoms, or

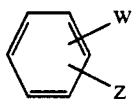

R² is R¹, NO₂, CN, CO₂R¹,

or halo;
R³ is R¹ or

W, Y, Z independently are H, halo, alkyl of 1-3 carbon atoms, OR³, NO₂, CF₃, fluoroalkyl, CN, or N(R¹)₂; and
one of Het¹ or Het² is 2, 3, or 4-pyridyl or 2, 4, or 5-pyrimidinyl and the other is selected from
(a) 2, 3, or 4-pyridyl,
(b) 2, 4, or 5-pyrimidinyl,
(c) 2-pyrazinyl,
(d) 3, or 4-pyridazinyl,
(e) 3, or 4-pyrazolyl,
(f) 2, or 3-tetrahydrofuranyl, and
(g) 3-thienyl.
Preferred compounds of Formula (III) are:
(a) those of Formula (III) where:
a is a single bond; and
X independently is O, CR¹R², or C(R¹)OR³;
W, Y and Z independently are H or OCH₃; or
Q is =O, =S, H₂, OR³, =CR¹R², or C(R¹)OR³; or
Het¹ and Het² are as preferred for compounds of Formula (I).
Specifically preferred compounds of Formula (III) from (a) above where a is a single bond are:
(i) 4-((2,3-dihydro-3-phenyl-1-(4-pyridinylmethyl)-1H-inden-1-ylmethyl))-pyridine dihydrochloride;
(ii) 1,1-bis(4-pyridinylmethyl)-1,3-dihydro-2H-inden-2-one,
(iii) 3,3-bis(4-pyridinylmethyl)-2,3-dihydro-1-phenyl-1H-indene-1,2-dioldiacetate dihydrochloride;
(iv) 3,3-bis(4-pyridinylmethyl)-2(3H)-benzofuranone dihydrochloride.
(b) those of Formula (III) where:
a is a double bond; and
X independently is CR²; or
W, Y and Z independently are H or CH₃; or Q is R²; or
Het¹ and Het² are as preferred for compounds of Formula (I).

A specifically preferred compound of Formula (III) from (b) above where a is a double bond is: 1,1-bis(4-pyridinyl-methyl)-3-phenyl-1H-indene-bismethanesulfonate.
(c) those of Formula (III) where:
a is a single bond; and
X and Y are taken together; and
Q is =O, =S, H₂, =CR¹R², or C(R¹)OR³; or
W and Z are each H or OCH₃; or
Het¹ and Het² are as preferred for compounds of Formula (I).
Specifically preferred compounds of Formula (III) from (c) above are:
(i) 2,2-bis(4-pyridinylmethyl)-1(2H)acenaphthylenone dihydrochloride;
(ii) 4-((1,2-dihydro-2-methylene-1-(4-pyridinylmethyl)1-acenaphthylene-1-ylmethyl)) pyridine dihydrochloride.
Compounds of Formula (IV) which can be used to practice the invention include those wherein a is a single bond or double bond;
b is a single bond or double bond, provided one of a or b is a single bond;
X independently when a and b are single bonds is O, S, CR¹R², CQ, C(R¹)OR³, or —(—CH₂—)—ₙ where n is 1, 2 or 3, N(CH₂)ₚR³ where p is 0 or 1, or NCOR¹;
X independently when one of a or b is a double bond is CR², COR³, or N;
V independently when b is a single bond is CQ;
V independently when b is a double bond is CR² or COR³;
A is a single bond, $+CR^1_2+_n$, —X—, $+CR^1_2+_n X$, where n is 1, 2 or 3 and X is as defined above when a is a single bond;
X and V taken together when A and b are single bond is

—CH ≠ CH ≠ CH=CH—;
   W      Z

Y and V taken together when A is a single bond is —CH₂—(—CH₂—)ₘ—CH₂— where m is 1 or 2;
provided that when X and V are connected, then V and X are not connected;
V and X taken together when b is a double bond is C—CH=CH—CH=CH—C—, or —C—(—CH₂—)-ₚ—C;
provided that when V and X are connected, then Y and V are not connected;
Q when a is a single bond is =O, =S, H₂, OR³, =NOR¹,

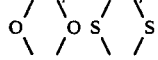

F₂, (R¹)OR³, =CR¹R²;
Q when a is a double bond is R², OR³ or halo;
p is 2 or 3;
R¹ is H, alkyl of 1-10 carbon atoms, cycloalkyl of 3-8 carbon atoms, or

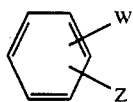

$R^2$ is $R^1$, $NO_2$, $CN$, $CO_2R^1$,

or halo;

$R^3$ is $R^1$ or

W, Y, Z independently are H, halo, alkyl of 1–3 carbon atoms, $OR^3$, $NO_2$, $CF_3$, fluoroalkyl, CN, or $N(R^1)_2$; and;

one of $Het^1$ or $Het^2$ is 2, 3, or 4-pyridyl or 2, 4, or 5-pyrimidinyl and the other is selected from
(a) 2, 3, or 4-pyridyl,
(b) 2, 4, or 5-pyrimidinyl,
(c) 2-pyrazinyl,
(d) 3, or 4-pyridazinyl,
(e) 3, or 4-pyradolyl,
(f) 2, or 3-tetrahydrofuranyl, and
(g) 3-thienyl.

Preferred compounds of Formula (IV) are:
(a) those of Formula (IV) where:
A is a single bond, and X and Y are taken independently; and
a and b are single bonds; or
Q is =O, =S, $=CR^1R^2$, $H_2$ or $C(R^1)OR^3$; or
X is $CR^1R^2$, O, or $NR_3$; or
V is $-CH_2-$, CQ, or $CR^1$; or
W, Y and Z each is H or $OCH_2$; or
$Het^1$ and $Het^2$ are as preferred for compounds of Formula (I); or
$R^1$ is H, $CH_3$ or phenyl; or
$R^2$ is H; or
$R^3$ is H

Specifically preferred compounds of Formula (IV) from (a) above, where a and b are single bonds are:
(i) 1,1-bis(4-pyridinylmethyl)-2-(1H)-naphthalenone; 4-bis(4-pyridinylmethyl)-2-phenyl-1,3(2H, 4H)isoquinolinedione.

(b) those of Formula (IV) where:
A is a single bond, and X and Y are taken independently; and
a is a single bond and b is a double bond; or
Q is $H_2$ or =O; or
X is N or $CR^2$; or
V is $CR^2$; or
W, Y and Z each is H or $OCH_3$; or
$Het^1$ and $Het^2$ are as preferred for compounds of Formula (I); or
$R^2$ is H or phenyl.

A specifically preferred compound of Formula (IV), from (b) above, where a is a single bond and b is a double bond is: 4,4-bis(4-pyridinylmethyl)-3,4-dihydro-6,7-dimethoxy-1-phenyl isoquinoline.

(c) those of Formula (IV) where:
A is a single bond, and Y and V are taken together, and b is a single bond; and
a is a single bond; or
Q is =O, =S, $=CR^1R^2$, or $C(R^1)OR^3$; or
X is $CR^1R^2$, O, or $NR^3$;
W and Z each is H or $OCH_3$; or
$Het^1$ and $Het^2$ are as preferred for compounds of Formula (I); or
$R^1$ is H, $CH_3$ or phenyl; or
$R^2$ is H; or
$R^3$ is H,

or phenyl.

A specifically preferred compound of Formula (IV), from (c) above, where a is a single bond is: 3,3-bis(4-pyridinylmethyl)-naphtho[1,8-b,c]pyran-2-one.

(d) those of Formula (IV) where:
V and X are taken together, and a is a single bond, and b is a double bond; and
A is $(CH_2)_n$, $(CH_2)_n-X$ where X is O, S, $SO_2$,

or $NH^3$ where $R^3$ is H, alkyl of 1–3 carbon atoms or acyl, and n is 0, 1 or 2; or
Q is =O, =S, $=CR^1R^2$, ir $C(R^1)OR^3$; or
W, Y and Z each is H or $OCH_3$; or
$Het^1$ and $Het^2$ are as preferred for compounds of Formula (I); or
$R^1$ is H, $CH_3$ or phenyl; or
$R^2$ is H; or
$R^3$ is H or

A specifically preferred compound of Formula (IV), from (d) above, is: 11,11-bis(4-pyridinylmethyl)-5-dibenzo[a,d] cyclohepten-10(11H)-one dihydrochloride.

The neurotransmitter enhancers mentioned above are described in and prepared by methods set forth in Applicants' Assignee's co-pending application U.S. Ser. No. 07/234,382, filed Aug. 23, 1988 and in Applicants' Assignee's European Patent Application Publication No. 0,311,010, published on Apr. 12, 1989.

The combination treatment of the invention can be administered by any conventional means available for use in conjunction with pharmaceuticals, either as individual therapeutic agents or in a combination of therapeutic agents. They can be administered alone, but are generally administered with a pharmaceutical carrier selected on the basis of the chose route of administration and standard pharmaceutical practice.

The dosage administered will, of course, vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired. For use in the treatment of neurological dysfunction, a daily oral dosage of active ingredient can be about 0.001 to 100 mg/kg of body weight. Ordinarily a dose of 0.01 to 10 mg/kg per day in divided doses one to four times a day or in sustained release form is effective to obtain the desired results.

Dosage forms (compositions) suitable for administration contain from about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil was prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The following illustrates the practice of the invention:

EXAMPLES

Animals

Male Sprague-Dawley rats (Charles River Breeding Laboratories, Kingston, NY) weighing 150–180 gm were used. The animals were housed four per cage (26.0 W×45.0 L×20.0 H cm) with free access to food and water. They were maintained on a 12 hr light/dark cycle (lights on from 0600 to 1800 hr) at a room temperature of 22±1° C. with a relative humidity of 50%±10%. In each experiment rats were used once.

Apparatus

The experimental sessions were conducted in a two compartment PA box. One compartment, made of clear plastic with a perforated clear plastic floor, measured 21(L)×24.5(H) x 17(W) cm and was illuminated with a 60 watt incandescent light bulb placed 36 cm above the floor of the PA box. The other compartment, made of black plastic, measured 30.5(L)×20.3(H)×21.5(W) cm with a floor made of 4 mm stainless steel rods spaced 1.2 cm apart. A Coulbourn Instruments Grid Floor Shocker was connected to the steel rods providing a scrambled footshock. The two compartments were separated by a solenoid-operated slide door (Lafayette Instrument Co., Lafayette, IN). A Coulbourn Instruments Electronic Counter, activated by the opening or closing of the slide door, recorded acquisition and retention latencies. These latencies were defined as the time, in seconds, it took an animal to enter (all four paws on the grid floor) the dark compartment.

For memory disruption, rats were exposed to an hypoxic environment for 30 min immediately prior to PA training. The hypoxia chamber was constructed of clear plastic, measured 32.5(L)×22.5(H)×23(W) cm, and was continuously perfused with a gas mixture of oxygen and nitrogen. The flow rate was adjusted such that the gas turnover in the chamber was 15 liters per min. To determine the effects of different oxygen concentrations on PA retention, the rats were exposed to gas mixtures containing different percentages of oxygen (21%, 10%, 9%, 8%, 7% or 6.5%) supplemented with nitrogen for 30 min prior to PA training. Oxygen concentrations were continuously monitored in the hypoxia chamber with an oxygen sensor (Sensitron, Inc., Reading, PA).

Passive Avoidance Training

PA training began by placing the rat into the clear compartment of the two compartment PA box. Following a 10 sec delay, the slide door was raised; providing access to the dark compartment. Once the rat moved completely into the dark compartment, the slide door was lowered and, after a 10 sec delay, a 1.5 mA inescapable shock was applied to the grid floor for 3 sec. This was followed by an additional 10 sec period at the end of which the rat received another 3 sec shock (1.5 mA). The rats were immediately removed from the dark compartment after receiving the second shock, injected with vehicle or test compound and returned to their home cage. Rats not entering the dark compartment within 90 sec were removed from the study. Of the animals tested, 3% were removed from the study for not entering the dark compartment within the allotted time (90 sec) during acquisition training.

A retention test was given 4 hr later. It proceeded in the same manner as the training session except no shock was applied to the grid floor when the rats entered the dark compartment. During the retention test, the rats were provided access to the dark compartment for 300 sec.

To determine if active doses increased entry latencies by altering the rats ability to enter the dark chamber during the retention test, the highest effective dose of each compound was administered to separate groups of non-shocked rats. Entry latencies were measured 4 hrs later.

Drug Preparation and Administration

DuP 996 was synthesized at Du Pont. Ketanserin (Janssen, Belgium) were dissolved in 0.85% saline and administered subcutaneously in a volume of 1 ml/mg of body weight one min after PA training. All doses were calculated as the free base.

Data Analysis

Overall significance was calculated using the Kruskall-Wallis one way analysis of variance (ANOVA). Post hoc, median retention latencies were compared for vehicle controls and each treated group with a Mann-Whitney U test. Data for different doses were accumulated over several days with both non-hypoxic and hypoxic vehicle treated control groups included with each day's testing.

EXAMPLE 1

Enhanced Efficacy of DuP996 when Co-administered with Ketanserin

The median latency to enter the dark chamber following hypoxia decreased as the oxygen concentration in the hypoxia chamber decreased. That is at 21%, 10%, and 9% oxygen the latencies were at a maximum 300 sec. However, the retention latencies of rats after being exposed to 8, 7, and 6.5% oxygen for 30 min before PA training were reduced to 167, 130 and 43 sec, respectively (Table 1).

TABLE 1

| HYPOXIA-INDUCED DISRUPTION OF PASSIVE AVOIDANCE RETENTION | |
|---|---|
| OXYGEN CONCENTRATION | MEDIAN RETENTION LATENCY (SEC) |
| 21% | 300 |
| 10% | 300 |
| 9% | 300 |
| 8% | 167* |
| 7% | 130* |
| 6.5% | 43* |

*Significantly different from 21% oxygen; $P < 0.05$

DuP 996, when administered after training to animals exposed to hypoxia, significantly improved retention latencies at a single dose of 0.1 mg/kg s.c. (Table 2).

Ketanserin at 0.3 mg/kg s.c. did not show a significant protective effect (Table 2).

TABLE 2

| EFFECT OF DuP 996 OR KETANSERIN ON HYPOXIA INDUCED RETENTION DEFICITS | | |
|---|---|---|
| | DOSE (mg/kg s.c.) | MEDIAN RETENTION LATENCY (sec) |
| | No Hypoxia | 300 |
| | Hypoxia | 17 |
| DuP 996 | 0.1 | 90* |
| | 0.3 | 38 |
| | 1.0 | 44 |
| Ketanserin | 0.3 | 49 |

*Significantly different from hypoxia; $P < 0.05$

However, when ketanserin (0.3 mg/kg s.c.) was coadministered with DuP 996 (0.1, 0.3 and 1.0 mg/kg s.c.) the magnitude of effect with the active dose of DuP 996 (0.1 mg/kg s.c.) increased by 220%. In addition the two previously inactive doses of DuP 996 (0.3 and 1.0 mg/kg s.c.) showed significant reversal of the hypoxia induced amnesia (Table 3).

TABLE 3

| CO-ADMINISTRATION OF KETANSERIN AND DuP 996 ATTENUATES HYPOXIA INDUCED MEMORY DEFICITS | |
|---|---|
| DOSE (mg/kg s.c.) | MEDIAN RETENTION LATENCY (SEC) |
| Hypoxia | 17 |
| No Hypoxia | 300 |
| Ketanserin + DuP 996 | |
| 0.3 + 0.1 | 198* |
| 0.3 + 0.3 | 253* |
| 0.3 + 1.0 | 162* |

*Significantly different from hypoxia; $P < 0.025$

What is claimed is:

1. A method of treating a neurological dysfunction in a mammal comprising administering to the mammal a synergistic therapeutically effective amount of (a) at least one $5HT_2$ serotonin receptor antagonist; and (b) at least one neurotransmitter enhancer, said enhancer being a compound selected from the group consisting of compounds of the formula:

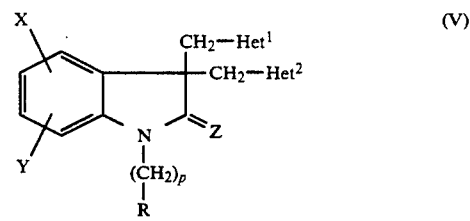

(V)

wherein:

p ps 0 or 1;

Z is O or S;

R is $C_1$-$C_{10}$ alkyl, $C_3$-$C_8$ cycloalkyl, 2-pyridyl, 3-pyridyl, 4-pyridyl, or

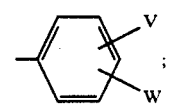

V, W, X, and Y independently are H, halo, $C_1$-$C_3$ alkyl, $OR^1$, $NO_2$, $CF_3$, CN, or $NR^1R^2$;

$R^1$ and $R^2$ independently are H or $C_1$–$C_3$ alkyl;

$Het^1$ and $Het^2$ independently are 6-membered heterocyclic aromatic rings containing one or two nitrogen atoms as part of the ring optionally substituted with one substituent selected from the group $C_1$–$C_3$ alkyl, halo, $OR^1$ or $NR^1R^2$; or an N-oxide or pharmaceutically suitable acid addition salt thereof.

2. The method of claim 1 wherein the neurotransmitter enhances (b) is 3,3-bis(4-pyridylmethyl)-1-phenylindolin-2-one.

* * * * *